United States Patent
Ghahfarokhi et al.

(10) Patent No.: US 11,678,946 B2
(45) Date of Patent: Jun. 20, 2023

(54) MAGNETIC COUPLING AND METHOD FOR CALIBRATING A ROBOTIC SYSTEM

(71) Applicant: Think Surgical, Inc., Fremont, CA (US)

(72) Inventors: Kamran Shamaei Ghahfarokhi, Fremont, CA (US); Feimo Shen, Fremont, CA (US); Barry Voorhees, Fremont, CA (US); Muhammad Afnan, Fremont, CA (US)

(73) Assignee: Think Surgical, Inc., Fremont, CA (US)

( * ) Notice: Subject to any disclaimer, the term of this patent is extended or adjusted under 35 U.S.C. 154(b) by 586 days.

(21) Appl. No.: 16/607,964

(22) PCT Filed: Apr. 17, 2018

(86) PCT No.: PCT/US2018/027938
§ 371 (c)(1),
(2) Date: Oct. 24, 2019

(87) PCT Pub. No.: WO2018/200256
PCT Pub. Date: Nov. 1, 2018

(65) Prior Publication Data
US 2021/0113285 A1   Apr. 22, 2021

Related U.S. Application Data

(60) Provisional application No. 62/639,703, filed on Mar. 7, 2018, provisional application No. 62/489,070, filed on Apr. 24, 2017.

(51) Int. Cl.
*A61B 34/00* (2016.01)
*A61B 34/10* (2016.01)
(Continued)

(52) U.S. Cl.
CPC .............. *A61B 34/70* (2016.02); *A61B 17/00* (2013.01); *A61B 34/10* (2016.02); *A61B 34/30* (2016.02);
(Continued)

(58) Field of Classification Search
CPC ......... A61B 34/70; A61B 17/00; A61B 34/10; A61B 34/30; A61B 2017/0042;
(Continued)

(56) References Cited

U.S. PATENT DOCUMENTS

| 1,859,352 | A | * | 5/1932 | Albee | A47G 7/041 |
| | | | | | 384/615 |
| 6,033,415 | A | * | 3/2000 | Mittelstadt | A61B 90/36 |
| | | | | | 600/425 |

(Continued)

FOREIGN PATENT DOCUMENTS

| EP | 0326768 A2 | 8/1989 |
| EP | 1016506 A1 | 7/2000 |

(Continued)

OTHER PUBLICATIONS

Langnau; Leslie. (Feb. 12, 2012). New Ways to Fasten. Design World Online (Year: 2012).*

(Continued)

*Primary Examiner* — Jonathan L Sample
*Assistant Examiner* — Elizabeth Rose Neleski
(74) *Attorney, Agent, or Firm* — MaxGoLaw PLLC

(57) ABSTRACT

An apparatus for calibration of a robotic arm having an end effector of a robot includes a magnetic coupler having a body, a receiving face, a mounting member, and a magnetic portion. The mounting member is configured to fixedly connect to the end effector of the robotic arm. A mechanical digitizer probe having a ball and a handle are provided, where the ball is fixedly attached to a distal end of the handle and the ball is removably coupled to the magnetic coupler via the magnetic portion on the receiving face to form a rotatable ball and socket connection, and where a proximal end of the handle is adapted to be attached to a mechanical digitizer associated with the robot. A method for calibration of the robotic arm of a robot is also detailed.

18 Claims, 13 Drawing Sheets

(51) Int. Cl.
*A61B 34/30* (2016.01)
*A61B 17/00* (2006.01)
*B25J 9/16* (2006.01)

(52) U.S. Cl.
CPC ..... *B25J 9/1692* (2013.01); *A61B 2017/0042* (2013.01); *A61B 2017/00477* (2013.01); *A61B 2017/00725* (2013.01); *A61B 2017/00876* (2013.01); *A61B 2034/102* (2016.02); *A61B 2034/105* (2016.02)

(58) Field of Classification Search
CPC ........... A61B 2017/00477; A61B 2017/00725; A61B 2017/00876; A61B 2034/102; A61B 2034/105; A61B 2034/2068; A61B 34/73; B25J 9/1692; B25J 9/0084; G05B 2219/39048; G05B 2219/39034
See application file for complete search history.

(56) References Cited

U.S. PATENT DOCUMENTS

| | | | | |
|---|---|---|---|---|
| 8,457,790 B2* | 6/2013 | Blondel | ................ | A61B 34/77 700/254 |
| 8,632,064 B2* | 1/2014 | Salisbury, Jr. | ......... | A61B 90/50 269/71 |
| 2002/0087233 A1 | 7/2002 | Raab | | |
| 2008/0188986 A1* | 8/2008 | Hoppe | ................... | B25J 9/1692 901/41 |
| 2011/0283815 A1 | 11/2011 | Langhans | | |
| 2011/0320153 A1 | 12/2011 | Lightcap et al. | | |
| 2013/0079928 A1* | 3/2013 | Soe-Knudsen | .......... | B25J 9/009 700/254 |
| 2014/0222207 A1* | 8/2014 | Bowling | ................ | A61B 17/16 700/261 |
| 2015/0051735 A1 | 2/2015 | Tanaka | | |
| 2017/0020613 A1 | 1/2017 | Kang et al. | | |

FOREIGN PATENT DOCUMENTS

| | | | | |
|---|---|---|---|---|
| KR | 10-2013-0005586 A | 1/2013 | | |
| WO | 2011008828 A2 | 1/2011 | | |
| WO | WO-2016020773 A1 * | 2/2016 | ............ | A61B 34/37 |
| WO | 2016-130946 A1 | 8/2016 | | |

OTHER PUBLICATIONS

University of Florida Mechanical and Aerospace Engineering Design and Manufacturing Laboratory, "Design for Manufacturing & Assembly (DFMA) Tips", 2017, University of Florida (Year: 2017).*
Suppl. Partial ESR for EP18791181, dated Apr. 19, 2021.
Int'l. Search Report for PCT/US2018/027938, dated Aug. 3, 2018.
Suppl. Partial ESR for EP18791181, Dec. 11, 2020.

* cited by examiner

S110: Magnetically couple a mechanical digitizer arm to an end-effector flange of a robotic arm

S120: Manipulate the robotic arm to a plurality of calibration locations

S130: record a set of joint values of the robotic arm at each calibration location

S140: measure, with the digitizer, a spatial position of the end-effector flange at each calibration location

S150: identify a set of kinematic parameters of the robotic arm with a calibration algorithm utilizing the set of joint values and the spatial position recorded and measured at each calibration location

S160: implement the set of robot kinematic parameters to complete the calibration of the robotic arm

FIG. 3

MAGNETIC COUPLING AND METHOD FOR CALIBRATING A ROBOTIC SYSTEM

RELATED APPLICATIONS

This application claims priority benefit of U.S. Provisional Application Ser. No. 62/639,703 filed 7 Mar. 2018; and U.S. Provisional Application Ser. No. 62/489,070 filed 24 Apr. 2017; the contents of which are hereby incorporated by reference.

FIELD OF THE INVENTION

The invention relates generally to the field of computer-assisted orthopedic surgery, and more specifically to a system and method for calibrating and diagnosing one or more components of a robotic system.

BACKGROUND OF THE INVENTION

Autonomous computer-aided surgical systems generally include a robotic arm attached to a base. The robotic arm performs a set of instructions created either pre-operatively or intra-operatively to aid the user in performing a particular medical procedure. One such system is the ROBODOC™ Surgical System (THINK Surgical, Fremont, Calif.) that aids a user in precisely milling the cavity of a femur to receive an implant in total hip arthroplasty (THA). As shown in prior art FIGS. 1A and 1B, the ROBODOC™ Surgical System 100 generally includes a robotic base 140, a robotic arm 150 having various links and joints, an end-effector flange 170, a mechanical digitizer 120, and a robot computing system 160. The end-effector flange 170 is located on a distal link of the robotic arm 150 and is adapted to attach one or more different end-effectors 180 to the robotic arm 150. The system 100 further includes two bone motion monitors (145a, 145b) (BMMs) positioned on either side of the system 100 which connect to the bone and monitor bone motion during the procedure. The mechanical digitizer 120 is removably mounted on the base 140 and calibrated relative to the robotic arm 150 such that the digitizer 120 can collect points on a bone intra-operatively to register the position and orientation (POSE) and coordinate transforms of the bone, a surgical plan, and the robotic arm 150 as described in U.S. Pat. No. 6,033,415.

To ensure the bone cavity is created accurately, the robotic arm 150, the mechanical digitizer 120, and tools all should be within tight operating parameters. Generally, the robotic arm 150 and the mechanical digitizer 120 are calibrated by the manufacturer when first installed at a customer site. The kinematic parameters (e.g., Denavit-Hartenberg (DH) parameters or modified DH parameters) are updated to account for any errors including joint-level errors, kinematic modeling errors, and non-geometric errors. Subsequently, prior to each medical procedure, the calibration is verified (i.e., diagnostics are performed) to ensure the system is operating within a specified accuracy tolerance.

As shown in FIG. 2, the calibration method is generally an integrated process of modeling 200, measurement 202, identification 204, and implementation 206 of the robot kinematic parameters. More detailed descriptions of each robotic calibration step can be found in the literature, including: Mooring et al., "Fundamentals of manipulator calibration," 1991 and in Elatta et al., "An Overview of Robot Calibration," Information Technology Journal 3 (1): 74-78, 2004.

Many different external measuring devices and methods are used to calibrate or verify the calibration of a robotic arm 150 including touching the tool tip to reference parts, laser triangulation, and calipers. As many of these techniques have been employed on industrial robots, their use in computer-aided surgical systems is limited due to the surgical setting and strict regulatory requirements. For example, the ROBODOC™ Surgical System 100 utilizes a reference plate. The reference plate has multiple reference points that are spaced a known distance apart within very tight tolerances. The robotic arm 150 is guided to the center of each of the reference points. The position of the robotic arm 150 is recorded at each of these points based on the manufacturer kinematic parameters and the joint encoder values of the robot. The recorded positions between each of these points, and the known distance between each of the points are used to identify new kinematic parameters. However, these procedural steps are often time consuming and require additional hardware (i.e., reference parts, calibration probes, optical tracking systems). In addition, and specifically for the ROBODOC™ System 100, the mechanical digitizer 120 attached at the base 140 must be removed to provide the robotic arm 150 with enough workspace to reach and record enough reference points on the reference plate. Following the calibration of the robotic arm 150, the mechanical digitizer 120 is re-assembled to the base 140, where the coordinate transformation between the coordinate system of the mechanical digitizer 120 and the coordinate system of the robotic arm 150 is calculated such that the bone can accurately be registered in the coordinate system of the robotic arm 150. Currently, the calculation of the coordination transformation between the digitizer 120 and the robotic arm 150 is determined using the same reference plate, wherein the digitizer is manually guided to multiple reference points. All in all, the removal of the digitizer 120, calibration of the robotic arm 150, re-assembly of the digitizer 120, and then the determination of the coordinate transform between the digitizer 120 and robotic arm 150 is time consuming, on the order of several hours.

Thus, there is a need for an efficient and effective method for calibrating and diagnosing one or more components of a robotic system.

SUMMARY OF THE INVENTION

An apparatus for calibration of a robotic arm having an end effector of a robot includes a magnetic coupler having a body, a receiving face, a mounting member, and a magnetic portion. The mounting member is configured to fixedly connect to the end effector of the robotic arm. A mechanical digitizer probe having a ball and a handle are provided, where the ball is fixedly attached to a distal end of the handle and the ball is removably coupled to the magnetic coupler via the magnetic portion on the receiving face to form a rotatable ball and socket connection, and where a proximal end of the handle is adapted to be attached to a mechanical digitizer associated with the robot.

A method for calibration of a robotic arm of a robot includes magnetically coupling a mechanical digitizer arm to an end-effector of a robotic arm with the above detailed apparatus. The robotic arm is manipulated to a plurality of calibration locations and paused at each calibration location. A set of joint values for the robotic arm at each calibration location are recorded. A spatial position of the end effector at each calibration location is measured with a mechanical digitizer. A set of kinematic parameters of the robotic arm are measured with a calibration algorithm utilizing the set of joint values and the spatial position recorded and measured at each calibration location. The set of robot kinematic parameters are implemented to complete the calibration of the robotic arm.

BRIEF DESCRIPTION OF THE DRAWINGS

The present invention is further detailed with respect to the following drawings that are intended to show certain aspects of the present invention, but should not be construed as a limit on the practice of the present invention.

FIG. 3 is a flowchart depicting a method for robot calibration in accordance with embodiments of the invention;

FIG. 5A is a side view thereof, and FIG. 5B is a detailed view of the calibration apparatus;

FIG. 6B is a front view, FIG. 6C is a side view, and FIG. 6D is a rear view according to the embodiments of the invention;

FIG. 7B is a front view, and FIG. 7C is a rear view according to the embodiments of the invention;

FIG. 9B is a perspective view thereof, and FIG. 9C is a longitudinal cross-sectional view thereof.

DETAILED DESCRIPTION OF THE INVENTION

The present invention has utility as a system and method for calibrating a robotic arm. The system and method is especially advantageous for reducing the calibration time and simultaneously determining a coordinate transform between a mechanical digitizer and the robotic arm. As reference is made herein to the application of this method and system to the ROBODOC® system, it should be appreciated that any autonomous, semi-autonomous, or passive robotic system, either for medical or industrial applications can benefit from the device and methods disclosed herein.

The following description of various embodiments of the invention is not intended to limit the invention to these specific embodiments, but rather to enable any person skilled in the art to make and use this invention through exemplary aspects thereof.

All publications, patent applications, patents and other references mentioned herein are incorporated by reference in their entirety.

Unless indicated otherwise, explicitly or by context, the following terms are used herein as set forth below.

As used in the description of the invention and the appended claims, the singular forms "a," "an" and "the" are intended to include the plural forms as well, unless the context clearly indicates otherwise.

Also, as used herein, "and/or" refers to and encompasses any and all possible combinations of one or more of the associated listed items, as well as the lack of combinations when interpreted in the alternative ("or").

As used herein, the term "calibration" refers to the process of identifying more accurate kinematic parameters of a robotic arm (e.g., the relative position and orientation of the links and joints of the robotic arm).

As used herein, the term "mechanical digitizer" refers to a measuring device capable of measuring physical coordinates in three-dimensional space. A "mechanical digitizer" refers to a mechanical digitizer consisting of passive links and joints, such as the high-resolution electro-mechanical sensor arm described in U.S. Pat. No. 6,033,415.

Figure 1A:
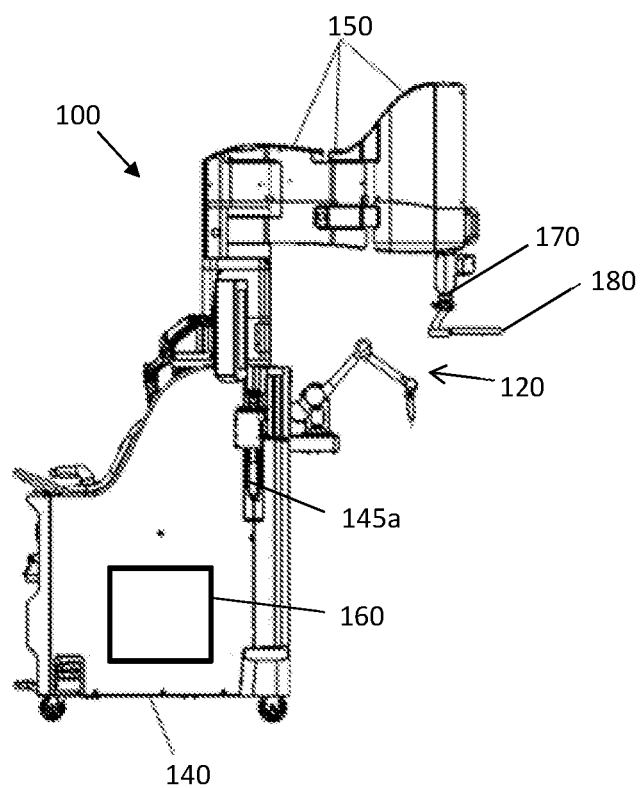
FIGS. 1A and 1B depict a front and side view, respectively of a prior art robotic system.

As shown and described above with reference to FIG. 1A, an "end-effector" 180 is shown as a tool attached to an end-effector flange 170. However, hereinafter, an "end-effector" broadly refers to a distal end of a distal link of a robotic arm. Under said definition, an "end-effector" now refers to: a) an end-effector flange; b) a tool attached to an end-effector flange; and/or c) an end-effector attachment device/mechanism/coupler with or without a tool attached thereto.

With reference now to the figures, in a particular inventive embodiment, with reference to FIG. 3, a method for calibrating a robotic arm 150 generally includes the steps of: (a) magnetically coupling a mechanical digitizer arm to an end-effector 180 of a robotic arm 150 (Block S110); (b) manipulating the robotic arm 150 to a plurality of calibration locations (Block S120); (c) recording joint values of the robotic arm 150 at each calibration location (Block S130); (d) measuring with the mechanical digitizer 120 a spatial position of the end-effector 180 at each calibration location (Block 140); (e) identifying a set of kinematic parameters of the robotic arm 150 with a calibration algorithm utilizing the set of joint values and the spatial position recorded and measured at each calibration location (Block S150); and (f) implementing the set of robot kinematic parameters to complete the calibration of the robotic arm 150 (Block S160). Specific embodiments of the system and method are further described below.

In a specific embodiment, a calibration apparatus (405, 405', 405"), as shown in FIGS. 5A-8C and further described in detail below, magnetically couples the mechanical digitizer 120 to an end effector flange 170 of the robotic arm 150. The calibration apparatus (405, 405', 405") ensures the digitizer 120 can rotate in three-degrees-of-freedom as the robotic arm 150 is manipulated to each calibration location without breaking the connection between the digitizer 120 and the robotic arm 150. The calibration apparatus (405, 405', 405") further includes components that provide a shared point of measurement for both the robotic arm 150 and the digitizer 120 during the measurement and/or recordation step in the calibration process.

Figure 4:
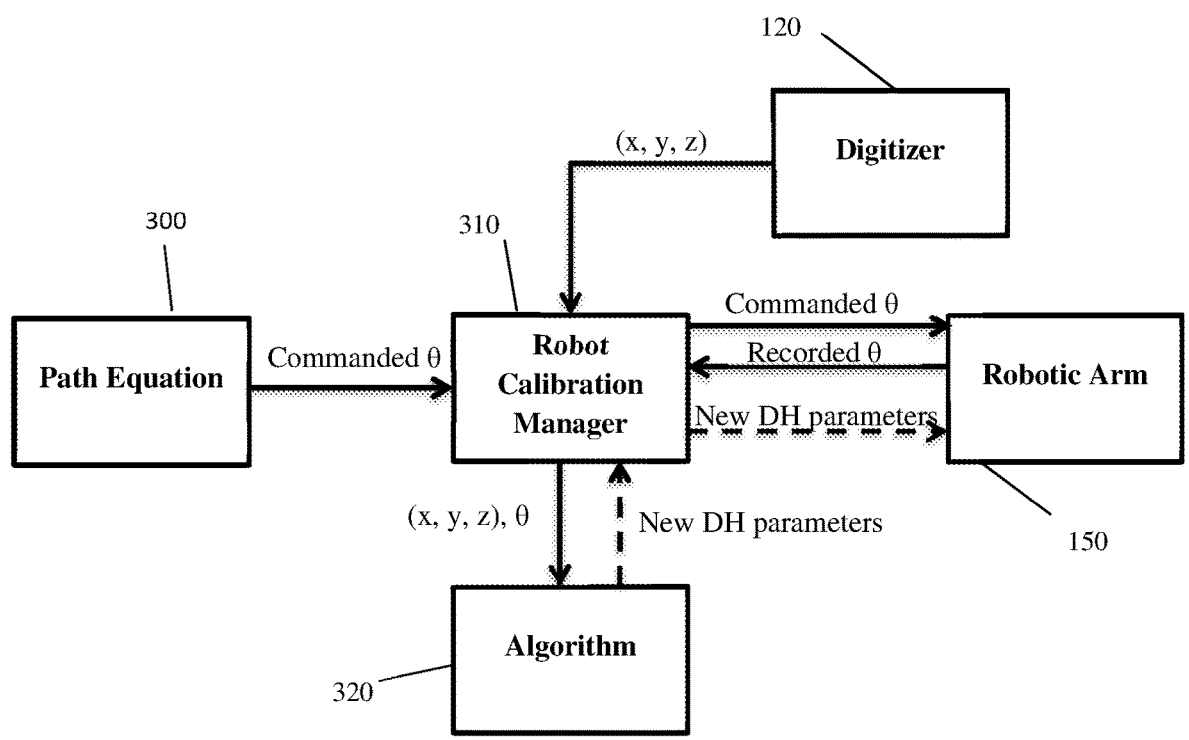
FIG. 4 is a functional block diagram of robot calibration procedure in accordance with embodiments of the invention.
Figure 5A:
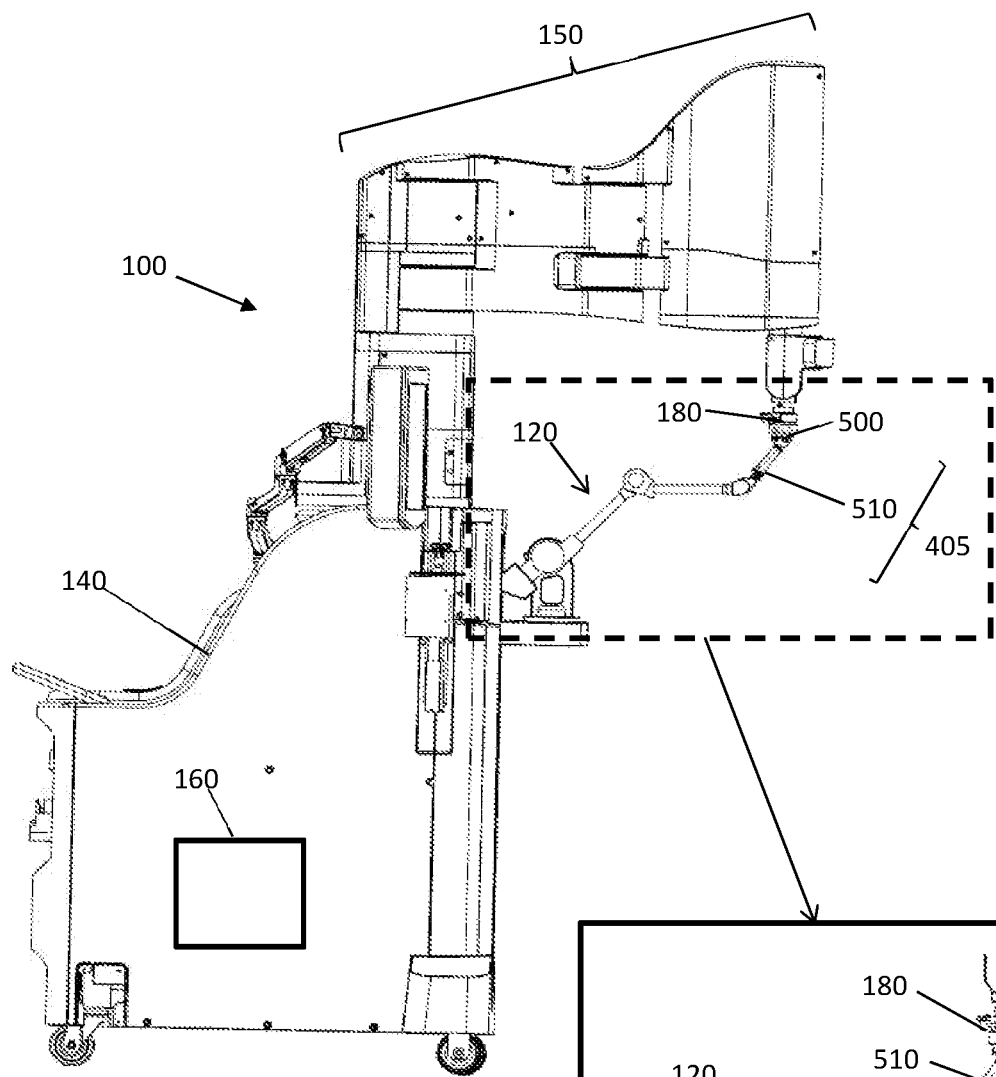
FIGS. 5A and 5B depict a robotic arm 150 coupled to a mechanical digitizer via a calibration apparatus in accordance with embodiments of the invention, where
Figure 5B:
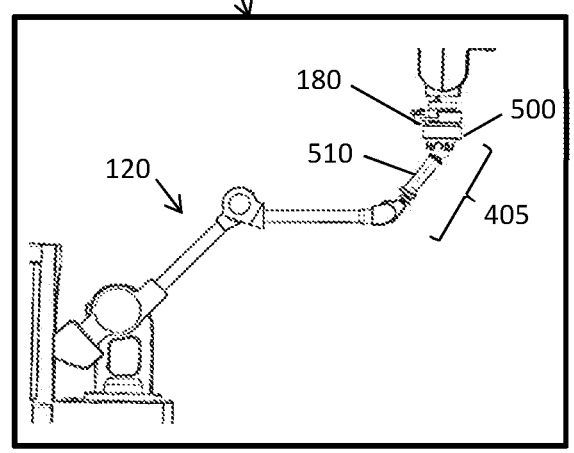

With reference to FIG. 4, a path equation 300 calculates each calibration location for the robotic arm 150 in accordance with step S120. More specifically, the path equation 300 determines multiple sets of joint commands to specify a plurality of calibration locations for the end effector flange 170 (FIG. 5A-5B). For example, the equation may calculate a first set of joint commands where a first joint is commanded to rotate to 15 degrees, a second joint is commanded to rotate to 80 degrees, and a third joint is commanded to translate to 20 cm, which positions the end-effector at a particular calibration location. While FIG. 4 references Cartesian coordinates, it is appreciated that the positions are readily determined in spherical or cylindrical coordinates. Each set of joint commands defines a calibration location, where the robotic arm 150 will pause while measurements are recorded. In a specific embodiment, the path equation 300 calculates the sets of joint commands to span the widest range of joint values without decoupling the robotic arm 150 from the mechanical digitizer 120. In a specific embodiment, at fifty or more calibration locations are calculated to calibrate the robot 100. However, it should be appreciated that fewer than fifty calibration locations may be calculated and used to obtain a desired calibration accuracy. The movement of the robotic arm 150 to any of the calibration locations in physical space is fully automatic, however it should be appreciated that a semi-automatic or a manual movement may also be used based on the application of this method.

In a specific embodiment, the mechanical digitizer 120 measures and records a spatial coordinate position (e.g., x, y, z) of the end-effector 180 at each calibration location. In a more specific embodiment, the mechanical digitizer 120 measures and records a spatial coordinate position (e.g., x, y, z) of a shared point between the end-effector 180 and the mechanical digitizer 120 at each calibration location relative to the mechanical digitizer 120 coordinate system. The location of the shared point is further described below with reference to the specific structure of the calibration apparatus (405, 405' 405"). At approximately the same time as the mechanical digitizer 120 measures and records the spatial coordinate position, the computing system 160 records the joint values of each robotic joint 150 via their respective joint encoders relative to the robotic arm 150 coordinate system. The recorded spatial position and corresponding joint values are stored for each calibration location. The set of joint values and spatial position recorded and measured at each calibration location may be stored in a database or other log file to consolidate all of the sets of joint values and corresponding spatial positions recorded and measured at all of the calibration locations. In a specific embodiment, the recorded joint values and spatial positions are sent and stored in a robot calibration manager software module 310.

The sets of joint values, as recorded by the computing system 160, and the spatial positions recorded and measured by the digitizer 120 are then transferred (e.g., transferring at least a portion of the database or log file) to an algorithm 320 to determine a set of new kinematic parameters for the robotic arm 150. The algorithm 320 may further determine a coordinate transformation between the coordinate system of the digitizer 120 and the coordinate system of the robotic arm 150. The algorithm 320 may be based on, but not limited to, linear least-squares parameter estimation, non-linear least-squares estimation, optimization, or Kalman Filtering. The coordinate transform may be determined by modeling the digitizer 120 as an extra link in the kinematic chain (i.e., the multiple links) of the robotic arm 150. The new kinematic parameters and/or coordinate transformation are then transferred to the robot computer 160 to complete the calibration of the robotic arm 150 (Block S160 of FIG. 3). The coordinate transformation between the coordinate system of the digitizer 120 and the coordinate system of the robotic arm 150 permits the digitizer to collect points on a bone, intra-operatively, to accurately register a bone, an image of a bone, and/or a surgical plan to the robotic arm 150. Once registered, the robotic arm may accurately perform a surgical procedure on the bone.

Calibration Apparatus

With reference to FIGS. 5A and 5B, an example of a robotic system 100 being calibrated by a calibration apparatus 405 is shown, where like reference numerals have the aforementioned meanings ascribed thereto. During the calibration procedure the calibration apparatus 405 couples the mechanical digitizer 120 to the end effector 180 to facilitate the measurement step in the calibration process.

Figure 6A:
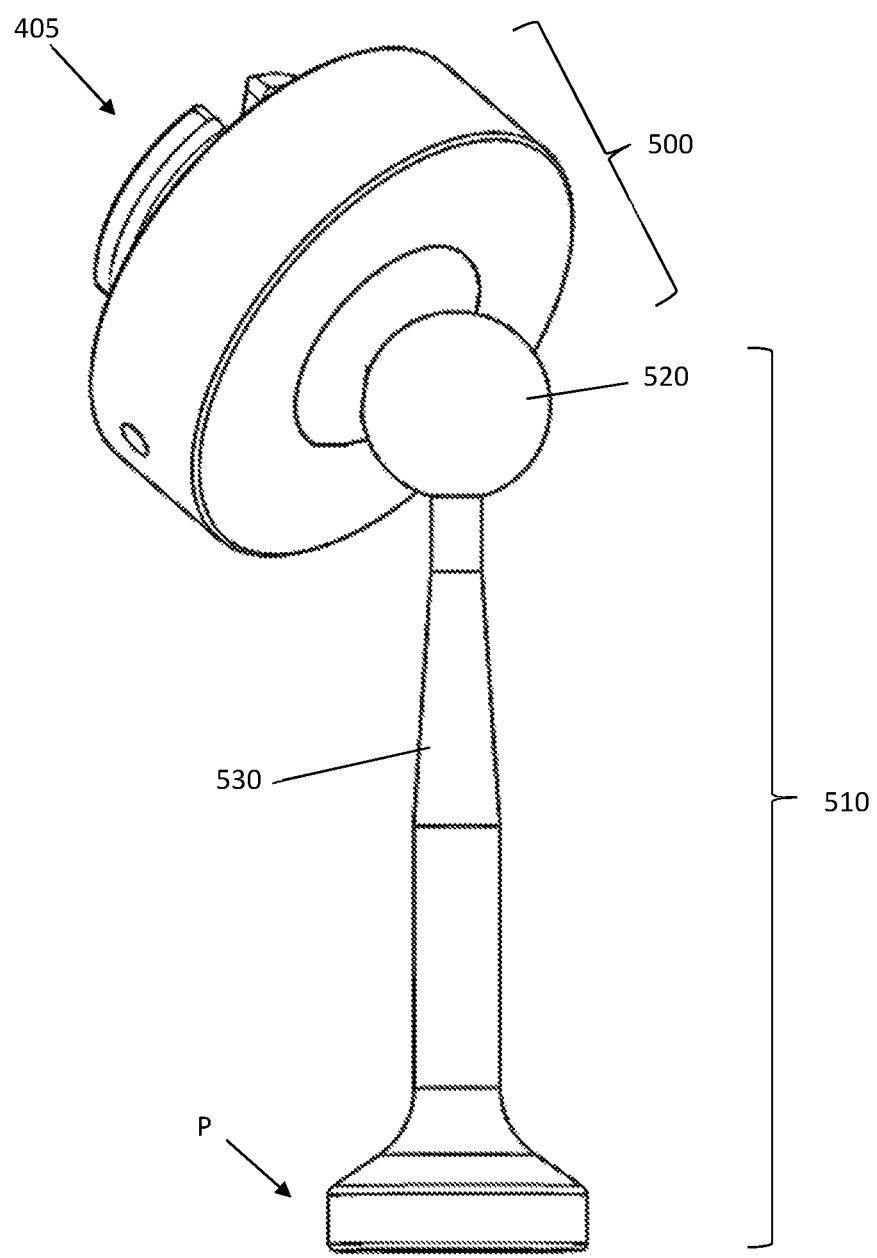
FIG. 6A is a calibration apparatus according to the embodiments of the invention.

With reference to FIG. 6A, a detailed view of a calibration apparatus 405 is shown. The calibration apparatus 405 includes a magnetic coupler 500 and a mechanical digitizer probe 510. The mechanical digitizer probe 510 includes a ball 520 and a handle 530. The ball 520 is configured to removably couple to the magnetic coupler 500 to form a rotatable ball and socket connection. The ball 520 may be made of material with ferromagnetic or paramagnetic properties such as steel, iron, or aluminum, as well as other materials known in the art. The handle 530 is configured to attach to a distal link of the mechanical digitizer 120. In a particular embodiment, the handle 530 includes a proximal end (P) having a fastening element for attaching the handle 530 to the distal link of the mechanical digitizer 120. The fastening element may include screw threads, a clamp, a binder, a clasp, a latch, a coupling, or a hook. In a specific embodiment, the handle 530 and the ball 520 is made from a single monolithic structure via known manufacturing techniques, while in other embodiments the handle 530 and the ball 520 are made of two or more separate pieces removably assembled with one or more fastening elements such as screwing, soldering, clamping, binding, or hooking.

Figure 6B:
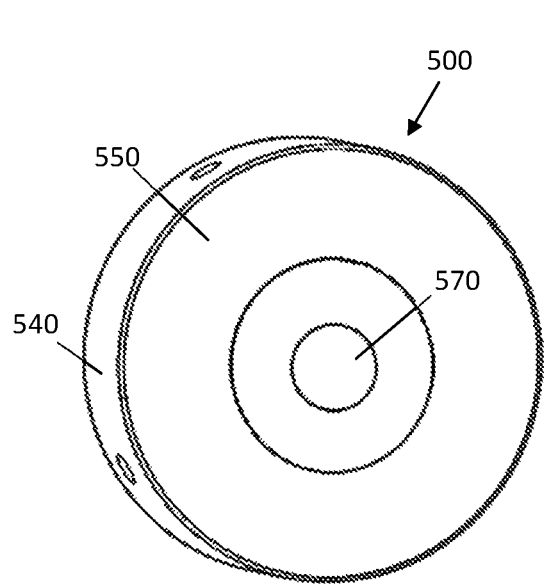
FIGS. 6B-6D depict a magnetic coupler of the calibration apparatus of FIG. 6A, where
Figure 6C:
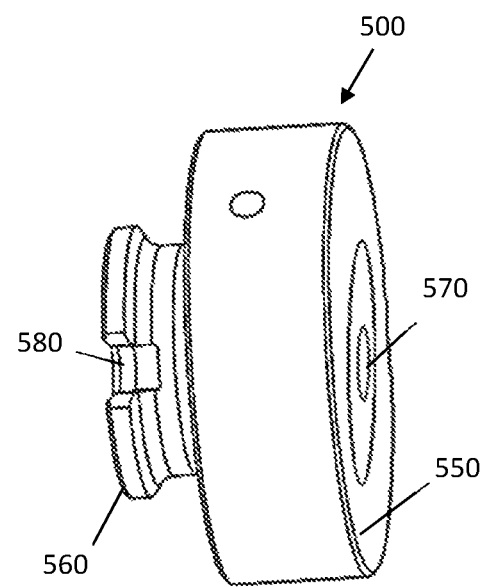
Figure 6D:
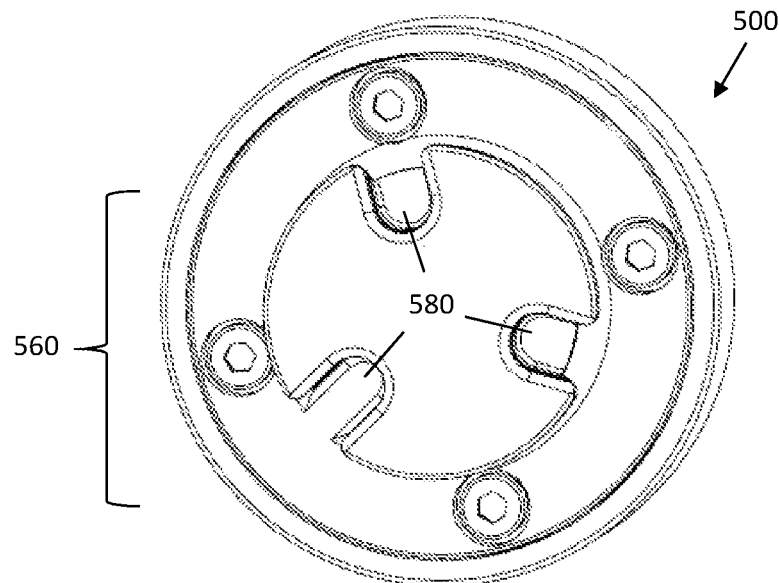

With reference to FIGS. 6B-6D, the magnetic coupler 500 is shown in more detail. In a specific embodiment, the magnetic coupler 500 includes a body 540, a receiving face 550 having a magnetic portion 570, and a mounting member 560. The magnetic portion 570 is configured to attract a portion of the ball 520 to the receiving face 550. In a particular embodiment, the magnetic portion 570 is formed with a magnet positioned in an interior part of the body 540 where at least a portion of the magnet is exposed on the receiving face 550. Magnetic forces between the ball 520 and magnetic portion 570 allows the movement of the mechanical digitizer probe 510 with three degrees of rotational freedom (e.g., pitch, roll, and yaw) while coupled to the magnetic coupler 500. The use of the magnetic coupler 500 is particularly advantageous as it allows the mechanical digitizer 120 and robotic arm 150 to work simultaneously, without detachment of the mechanical digitizer 120 from the robotic arm 150. Additionally, the simultaneous movements of the mechanical digitizer 120 and the robotic arm 150 allows for the determination of the coordinate transformation between the coordinate system of the mechanical digitizer 120 and the coordinate system of the robotic arm 150 while the calibration is progressing.

The mounting member 560 connects the magnetic coupler 500 to the robotic arm 150. In a specific embodiment, the mounting member 560 attaches to the end-effector 180 of the robotic arm 150. The mounting member 560 may have a shaft with threads, a clamping mechanism, or equivalents thereof, to attach the mounting member 560 and maintain a rigid relationship with the robotic arm 150. In a particular embodiment, as shown in FIG. 6C the mounting member 560 may further include a plurality of intrusions 580 adapted to receive a plurality of projections in the end-effector 180 to align the magnetic coupler 500 in a specific orientation on the end-effector 180.

Figure 7A:
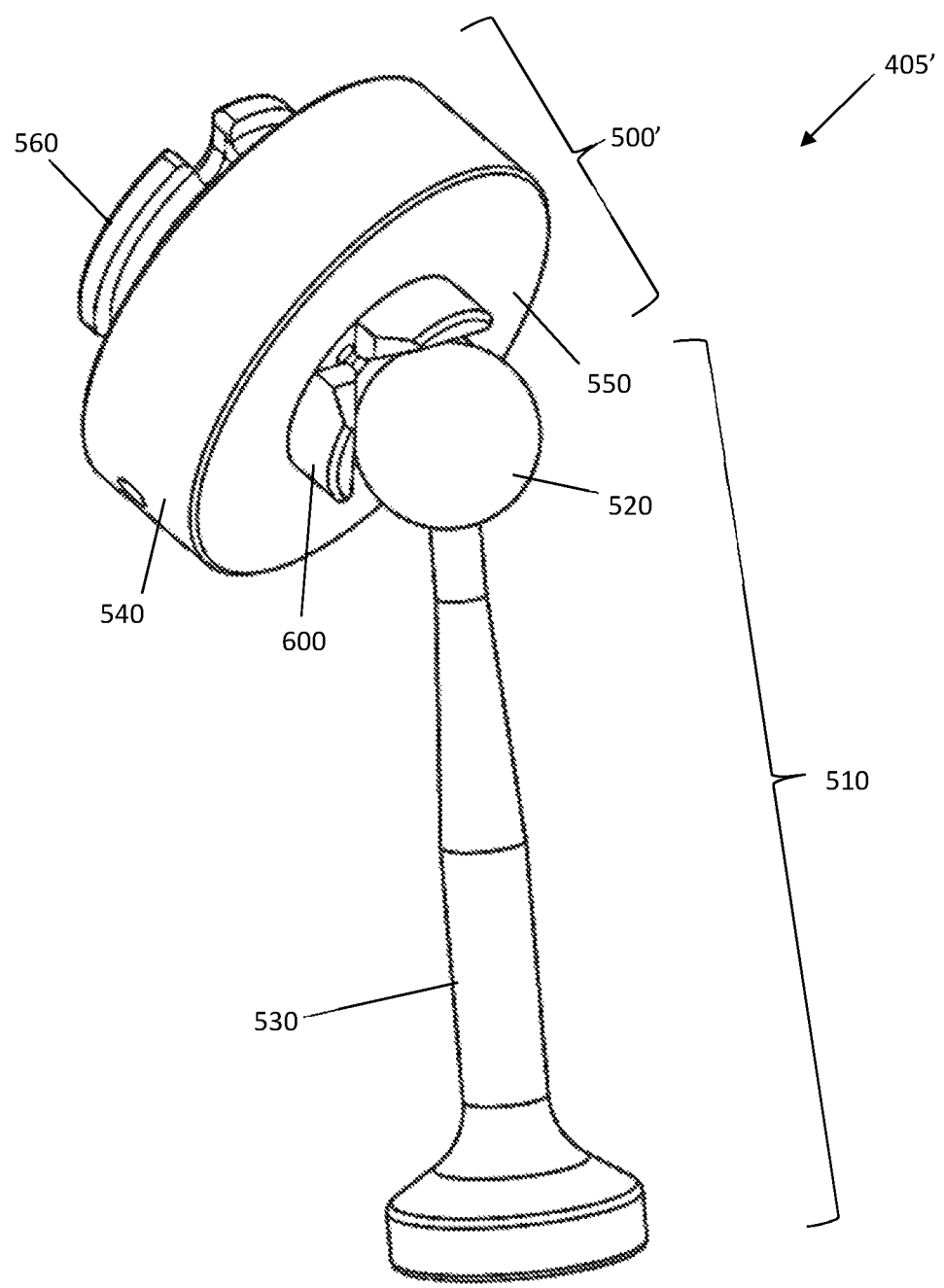
FIG. 7A is a calibration apparatus according to the embodiments of the invention.
Figure 7B:
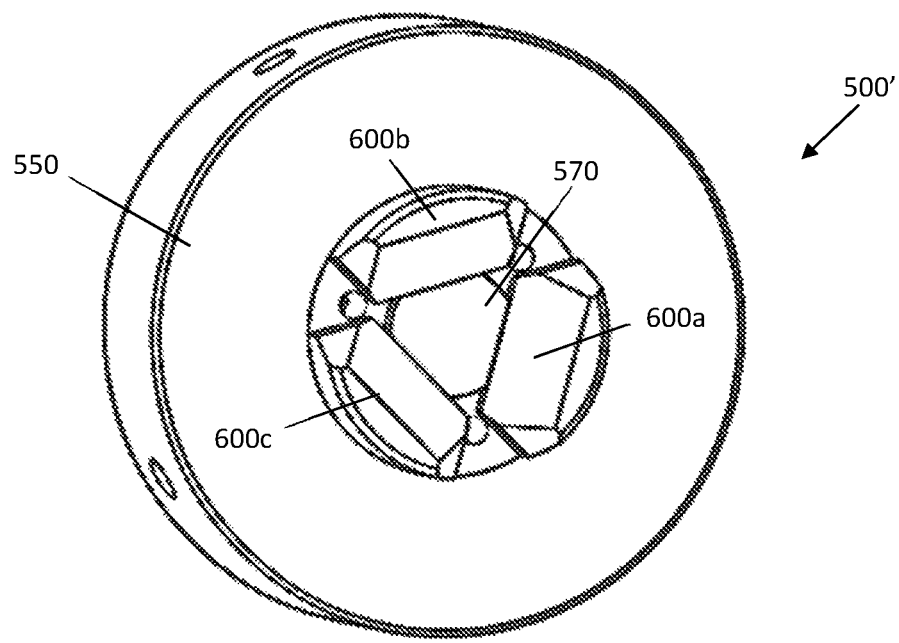
FIGS. 7B and 7C depict a magnetic coupler of the calibration apparatus of FIG. 7A, where
Figure 7C:
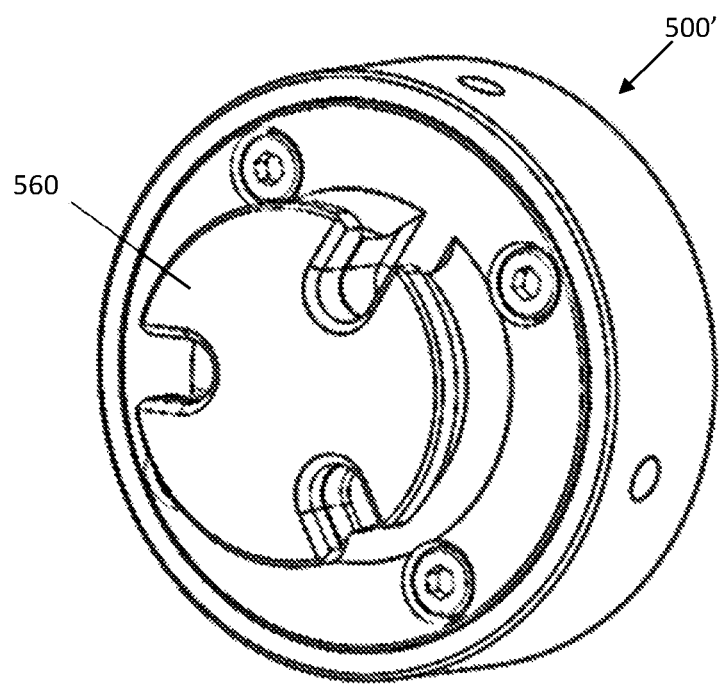

With reference to FIGS. 7A-7C, another embodiment of a magnetic coupler 500' is shown. The magnetic coupler 500' includes a plurality of supporting members 600 extending from the receiving face 550. In a specific embodiment, three supporting members (600a, 600b, 600c) project from the receiving face 550 in the form of a circle to form a receiving pocket in the center thereof in which the magnetic portion 570 is situated. Three supporting members 600 are advantageous as exactly three points can capture and stabilize the spherical ball 520, as the ball 520 rotates about the magnetic portion 570. The supporting members 600 may be in any shape or size for the desired application. The supporting members (600a, 600b, 600c) may further include an inner angled surface to capture the ball 520. In a specific embodiment, the shape of the supporting members (600a, 600b, 600c) is as shown in FIG. 7B where this particular shape allows the rotation of the ball 520 with the least amount of deviation from the center of the magnetic portion 570.

Figure 8A:
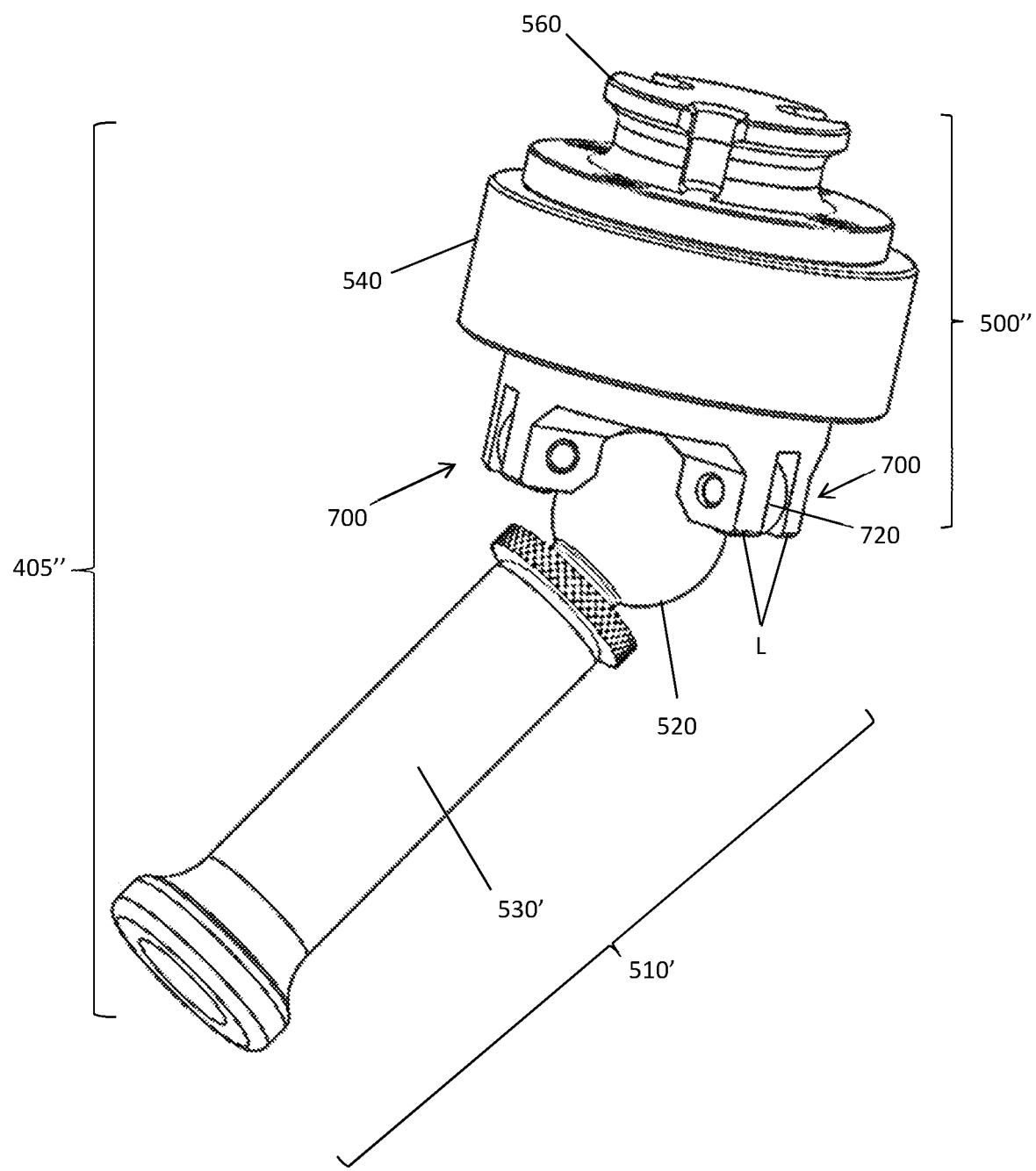
FIG. 8A is a calibration apparatus according to the embodiments of the invention.
Figure 8B:
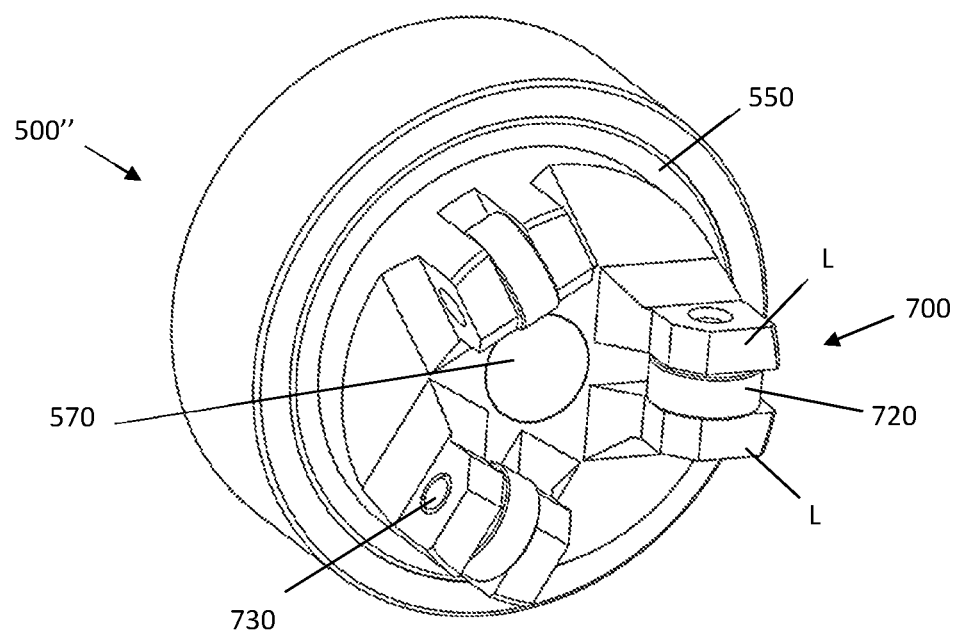
FIG. 8B is a front view of a magnetic coupler of the calibration apparatus of FIG. 8A according to the embodiments of the invention.
Figure 8C:
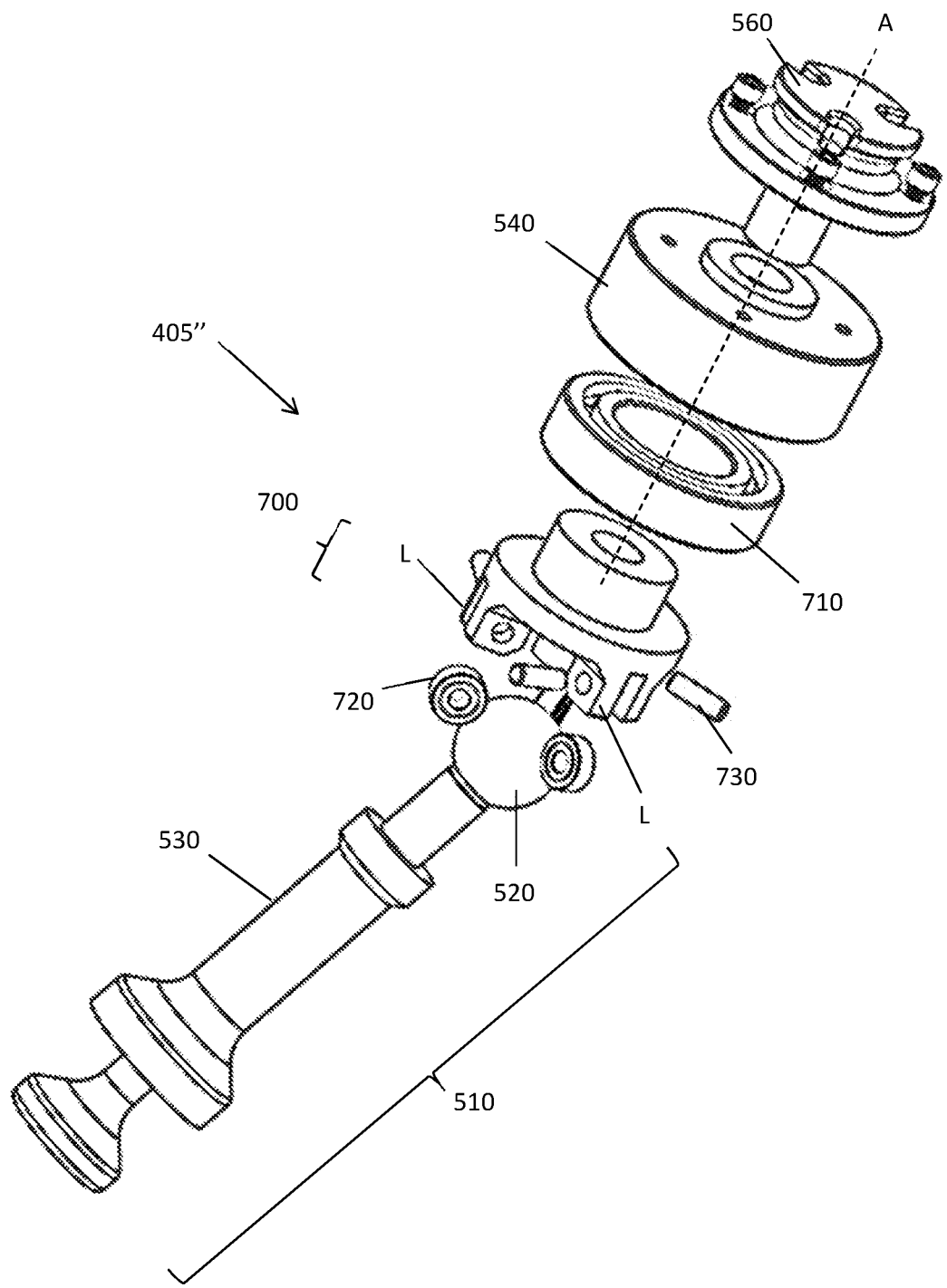
FIG. 8C is an exploded view of a calibration apparatus of FIG. 8A according to the embodiments of the invention.

Referring now to FIGS. 8A-8C, another embodiment of a magnetic coupler 500" is shown. The magnetic coupler 500" includes a plurality of supporting members 700 projecting from the receiving face 550 and at least one rotation bearing 710 positioned within the body 540. FIG. 8C depicts the magnetic coupler 500" in an exploded view, where the rotation bearing 710 is configured to allow the rotation of the receiving face 550 about a center axis (A) of the magnetic coupler 500". In a specific embodiment, each supporting member 700 includes a pair of legs (L) acting as a frame for a bearing/wheel 720. The bearing/wheel 720 is positioned between the pair of legs (L) and assembled thereto via a pin/axle 730. The bearing/wheel 720 is particularly advantageous as the bearings/wheels 720 decrease the friction between the ball 520 and the receiving face 550 and therefore increase the longevity of the calibrating apparatus 405".

The calibration apparatus (405, 405', 405") couples the mechanical digitizer 120 to the robotic arm 150 and is used during the measuring and recording steps (202, S130, S140) of the calibration procedure. In a specific embodiment, during the measuring step, the digitizer 120 measures the spatial position of the end-effector 180 as the center of the ball 520, which is considered the shared point between the robotic arm 150 and the digitizer 120 as mentioned above. The shared point ensures that the mechanical digitizer 120 and robotic arm 150 are measuring and recording with reference to the same point in space at each calibration location.

Figure 1B:
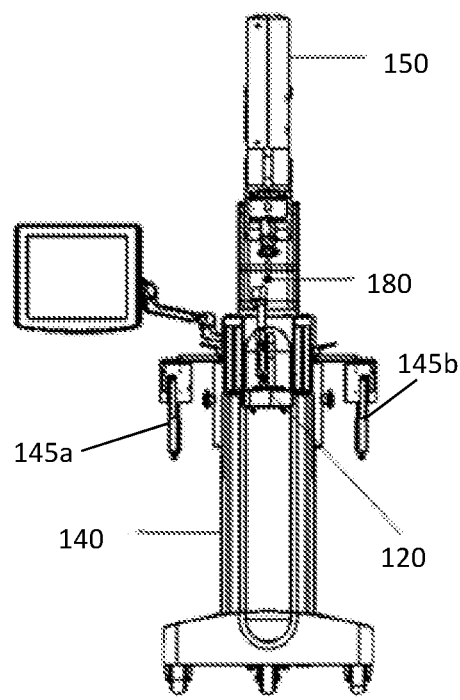
Figure 2:
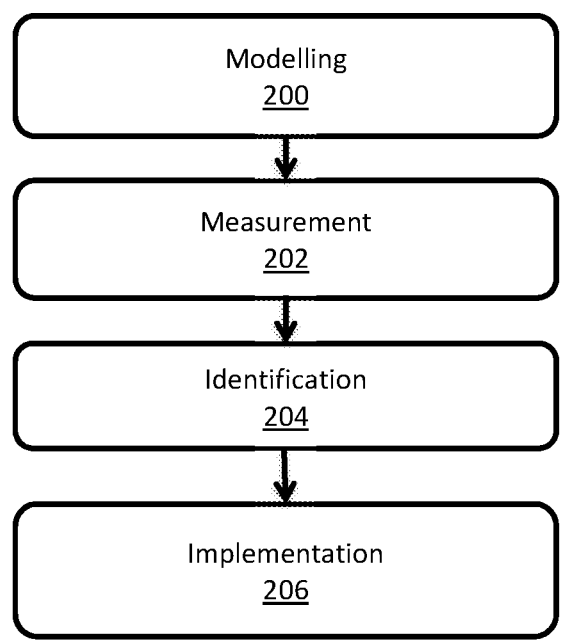
FIG. 2 is a flowchart depicting a general method of robotic calibration having inventive embodiments of sub-steps therein in accordance with embodiments of the invention.

With resort to the inventive calibration apparatus (405, 405', 405"), a robotic system is readily calibrated to a tolerance of 0.1±0.1 mm in a time of less than 5 minutes and in particular instances within a time of between 30 seconds and 10 minutes depending on how fast the robotic arm can move and how many data points (i.e., calibration locations) are needed for a desired accuracy. This is contrast to the system of FIGS. 1A and 1B in which, absent the inventive calibration apparatuses (405, 405', 405"), a calibration to the same tolerance requires approximately 4 hours. As a result of this greater speed of calibration, complete recalibration is now feasible between consecutive surgical procedures and intra-operatively thereby assuring a higher degree of surgical precision. As surgical precision is known to correlate with faster surgical recovery and longer implant longevity, a net savings to the medical system and better patient outcomes are achieved through resort to the present invention.

Bone Motion Monitor Diagnostics

Figure 9A:
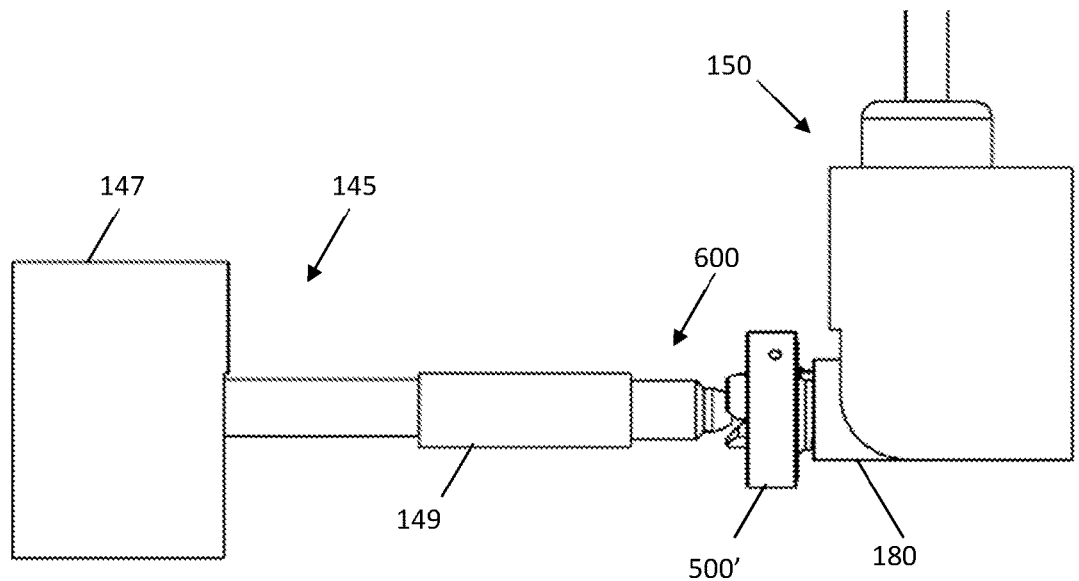
FIG. 9A depicts a bone motion monitor magnetically coupled to an end-effector by way of a diagnostic calibration apparatus to perform diagnostics on the bone motion monitor in accordance with embodiments of the invention.
Figure 9B:
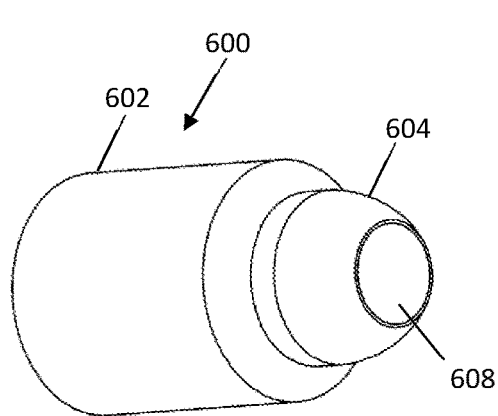
FIGS. 9B and 9C depict the diagnostic calibration apparatus as shown in FIG. 9A in accordance with embodiments of the invention, where
Figure 9C:
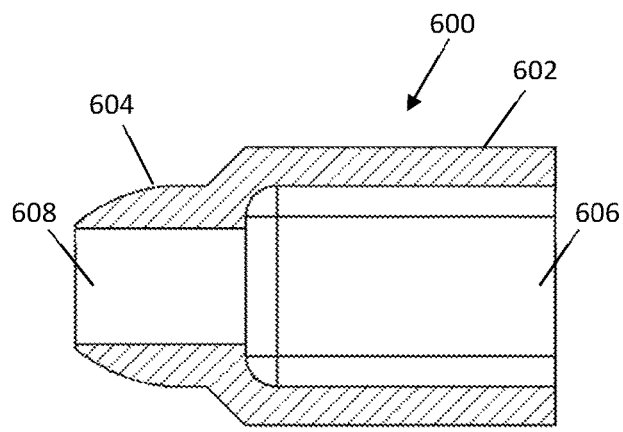

With reference to FIGS. 9A-9C, a diagnostic calibration apparatus 600 is shown to perform diagnostics on a bone motion monitor 145. The bone motion monitor 145 (BMM) includes three or more degrees-of-freedom to monitor and detect motion of a bone attached thereto during the surgical procedure. The BMM 145 generally includes a housing 147 having revolute joints, encoders, and other electrical components therein to detect rotational movement of the bone, and a prismatic joint/link 149 having a distal end that attaches to the bone to detect linear motion. The BMM 145 is a crucial component to the system because if the bone moves during the procedure, said movement will shift the bone cuts. Therefore, the BMM 145 detects any movement post-registration, 'freezes' cutting in the event of bone motion, and alerts the surgical team to recover the registration.

To ensure the BMM 145 is operating accurately and within the designated parameters, diagnostics is performed on the BMM 145. Conventionally, diagnostics on the BMM 145 is accomplished using a similar method as the reference plate. A probe attached to the BMM 145 is guided to specific divots on a 'reference plate', where those divots are spaced a known distance and orientation apart. The BMM records the position of the probe at each of those specific points and the distance and orientation between the recorded points should match within a certain degree of accuracy to the actual distance and orientation between the divots on the 'reference plate'. This is a very time-consuming process.

To improve BMM 145 diagnostics, the diagnostic calibration apparatus 600 is used. The diagnostic calibration apparatus 600 is an attachment for the distal end of the BMM 145, more specifically the distal end of the link 149, to facilitate the magnetic attachment of the BMM to the magnetic coupler (500, 500', 500"). The diagnostic calibration apparatus 600 is made of a ferrous metal to magnetically couple to the magnetic coupler (500, 500', 500"). In general, the diagnostic calibration apparatus 600 includes a first portion 602 and second portion 604. The first portion 602 assembles to the distal end of the BMM 145 (e.g., distal end of link 149) and the second portion 604 magnetically couples to the magnetic coupler (500, 500', 500"). In some embodiments, the first portion 602 is in the form of a cylinder having a rectangular hole 606 therethrough, said rectangular hole 606 mating with a male rectangular member associated with the distal end of the BMM 145. The second portion 604 is in the form of a dome having a cylindrical hole 608 therethrough. The rectangular hole 606 and cylindrical hole 608 permit a BMM probe (not shown) to be passed therethrough and assembled to the BMM 145. The BMM probe is the device that fixes directly on the bone such that the BMM 145 can monitor bone motion. Therefore, the diagnostic calibration apparatus 600 does not need to be removed after diagnostics.

The actual diagnostic procedure is as follows. First, the diagnostics calibration apparatus 600 is assembled to the distal end of the BMM 145 (the apparatus 600 may also be a permanent fixture since a BMM probe may still be attached to the BMM 145 through the apparatus 600). Next, the end effector 180 having the magnetic coupler (500, 500', 500") installed thereon is moved, automatically, to a known location and orientation near the BMM. A user is then instructed to move the BMM 145 to a known height and angle (the height may be adjusted by manually sliding the base 147 along a linear rail guide assembled to the robot base 140 and subsequently fastened into position). After which, the user is instructed to magnetically couple the calibration apparatus 600 to the magnetic coupler (500, 500', 500"). The robot arm 150 then automatically moves the BMM 145 to a plurality of different locations and orientations. In a particular embodiment, the BMM is moved to 6 or more locations and orientations. Points at each location and orientation are collected and compared to expected values. If the diagnostics passes, then the user is instructed to decouple the BMM 145 from the magnetic coupler (500, 500', 500") and the procedure continues. This diagnostic procedure is highly advantageous as there is minimal hardware required and the diagnostics can be completed between 1 and 5 minutes.

Other Embodiments

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes can be made in the function and arrangements of elements without departing from the scope as set forth in the appended claims and the legal equivalents thereof.

The invention claimed is:

1. An apparatus for coupling a digitizer to a robotic arm having an end-effector for facilitating the calibration of the robotic arm, the apparatus comprising:
   a first coupler comprising a mounting member and a receiving member; and
   a probe comprising a curved surface and a second coupler, wherein the curved surface is configured to couple to the receiving member and rotate relative to the receiving member as the robotic arm moves the end effector; and
   wherein the mounting member is configured to couple to the end-effector of the robotic arm, and the second coupler is configured to couple to a distal end of the digitizer.

2. The apparatus of claim 1 wherein the curved surface magnetically couples to the receiving member.

3. The apparatus of claim 1 wherein the mounting member comprises a plurality of intrusions to align the first coupler in a specific orientation on the end effector.

4. The apparatus of claim 1 wherein the first coupler further comprises a plurality of supporting members extending from said receiving member.

5. The apparatus of claim 1 wherein the first coupler further comprises at least one rotation bearing, wherein said at least one rotation bearing permits the receiving member to rotate relative to the mounting member.

6. The apparatus of claim 4 wherein at least one supporting member of said plurality of supporting members comprises a second bearing.

7. A method for calibrating a robotic arm of a robot, said method comprising:
   manipulating a robotic arm to a plurality of calibration locations, wherein a digitizer is coupled to an end-effector of the robotic arm with the apparatus of claim 1;
   recording joint values of the robotic arm at each calibration location;
   measuring, with said digitizer, a spatial position with respect to the end effector at each calibration location;
   identifying kinematic parameters of the robotic arm with a calibration algorithm utilizing the recorded joint values and the measured spatial position at each calibration location; and
   implementing the kinematic parameters to complete the calibration of the robotic arm.

8. The method of claim 7 further comprising determining multiple sets of joint commands, wherein each set of joint commands specify a calibration location for said end-effector.

9. The method of claim 8 wherein the measured spatial position with respect to the end-effector is a shared point between said robotic arm and said digitizer, wherein each spatial position is measured and recorded relative to a coordinate system of said mechanical digitizer, and wherein one or more computers records the joint values of the robotic arm in a coordinate system of said robotic arm.

10. The method of claim 9 wherein the calibration algorithm further determines a coordinate transformation between the coordinate system of the digitizer and the coordinate system of the robotic arm.

11. The method of claim 10 wherein the calibration algorithm is based on at least one of linear least-squares parameter estimation, nonlinear least-squares estimation, optimization, or Kalman Filtering.

12. The method of claim 10 wherein the coordinate transformation is determined by modeling the digitizer as one or more extra links of the robotic arm.

13. A robotic system, comprising:
   a robotic arm for moving an end-effector to a plurality of end-effector locations;
   a digitizer;
   the apparatus of claim 1 for coupling the end-effector and the digitizer; and
   a computer for receiving position data from the digitizer, the position data corresponding to a spatial position with respect to the end-effector at each of the plurality of end-effector locations.

14. The robotic system of claim 13 wherein the one or more computers receive joint values of the robotic arm at each of the plurality of end-effector locations.

15. The robotic system of claim 14 wherein the computer executes a calibration algorithm to determine kinematic parameters of the robotic arm using the position data from the digitizer and the joint values of the robotic arm.

16. The robotic system of claim 13 wherein the spatial position of the end-effector is a shared point between the digitizer and the robotic arm.

17. The robotic system of claim 13 wherein the curved surface magnetically couples to the receiving member.

18. The system of claim 13 wherein the first coupler further comprises at least one rotation bearing, wherein said at least one rotation bearing permits the receiving member to rotate relative to the mounting member.

\* \* \* \* \*